United States Patent
Knoepfle et al.

(10) Patent No.: US 9,717,489 B2
(45) Date of Patent: Aug. 1, 2017

(54) SURGICAL RETRACTOR

(75) Inventors: Christian Knoepfle, Donaueschingen (DE); Juergen Rettich, Muehlheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 229 days.

(21) Appl. No.: 13/993,113

(22) PCT Filed: Dec. 13, 2011

(86) PCT No.: PCT/EP2011/006285
§ 371 (c)(1),
(2), (4) Date: Jul. 30, 2013

(87) PCT Pub. No.: WO2012/079743
PCT Pub. Date: Jun. 21, 2012

(65) Prior Publication Data
US 2013/0331656 A1   Dec. 12, 2013

(30) Foreign Application Priority Data
Dec. 13, 2010 (DE) .................. 10 2010 054 333

(51) Int. Cl.
*A61B 1/32* (2006.01)
*A61B 17/02* (2006.01)

(52) U.S. Cl.
CPC ................ *A61B 17/0231* (2013.01)

(58) Field of Classification Search
CPC .. A61B 17/02; A61B 17/0206; A61B 17/0231
USPC ............. 606/205–211; 600/184–246
See application file for complete search history.

(56) References Cited

U.S. PATENT DOCUMENTS

| | | | |
|---|---|---|---|
| 5,070,860 A | 12/1991 | Grounauer | |
| 5,271,385 A | 12/1993 | Bailey | |
| 6,068,643 A | 5/2000 | Milverton | |
| 6,283,913 B1 * | 9/2001 | Seibel ................. | A61B 1/32 600/219 |
| 6,544,169 B2 | 4/2003 | Putrino et al. | |

(Continued)

FOREIGN PATENT DOCUMENTS

| | | |
|---|---|---|
| DE | 69120325 T2 | 12/1996 |
| DE | 29804127 U1 | 5/1998 |

(Continued)

OTHER PUBLICATIONS

Fernandes, "Rapid Response: Fernandes Orbital Retractor", www.biometmicrofixation.com, 2011.

(Continued)

*Primary Examiner* — Ellen C Hammond
*Assistant Examiner* — Christina Negrellirodrigue
(74) *Attorney, Agent, or Firm* — Lerner, David, Littenberg, Krumholz & Mentlik, LLP

(57) ABSTRACT

A retractor (10) for use in a surgical intervention in the area of an eye socket is described. The retractor (10) comprises two planar retraction elements (26, 28), which are movable relative to each other between an insertion position with a first surface coverage and a retraction position with a second surface coverage AI, which is smaller than the first surface coverage. A spring element (20) provides pretensioning, which presses the retraction elements (26, 28) into the retraction position.

20 Claims, 4 Drawing Sheets

(56) References Cited

U.S. PATENT DOCUMENTS

| | | | |
|---|---|---|---|
| 2002/0103421 A1 | 8/2002 | Putrino et al. | |
| 2005/0267336 A1* | 12/2005 | Bertolero | A61M 1/3659 600/219 |
| 2008/0081952 A1 | 4/2008 | Josephberg | |
| 2011/0098538 A1* | 4/2011 | Terry | A61B 17/0231 600/236 |

FOREIGN PATENT DOCUMENTS

| | | |
|---|---|---|
| EP | 2201899 A1 | 6/2010 |
| WO | 2011053945 A2 | 5/2011 |

OTHER PUBLICATIONS

Inernational Search Report for Application No. PCT/EP2011/006285 dated Mar. 5, 2012.
Raveh, "Leibinger: Instrumentation for Fronto-Orbital and Anteroposterior Skull Base Procedures", Copyright 1996.

* cited by examiner

SURGICAL RETRACTOR

CROSS-REFERENCE TO RELATED APPLICATIONS

The present application is a national phase entry under 35 U.S.C. §371 of International Application No. PCT/EP2011/006285 filed Dec. 13, 2011, published in German, which claims priority from German Patent Application No. 10 2010 054 333.0 filed Dec. 13, 2010, all of which are incorporated herein by reference.

TECHNICAL FIELD

The present disclosure relates to the field of surgical instruments. More precisely, a retractor for use in a surgical operation in the region of an eye socket is presented. Because the eye socket is also referred to as the orbit, such retractors are known as what are called orbital retractors.

BACKGROUND

Retractors are generally used within the scope of a surgical operation in order to allow access to the operation field or to keep it open. Therefore, in the case of a fracture of the eye socket floor, the soft tissue that fills the eye socket must be pushed back by means of an orbital retractor, before the fracture can be treated. Conventionally, spatula-shaped or spoon-shaped retractors are used in this connection.

An orbital retractor in spoon shape is known from EP 2 201 899 A1 and US 2008/0081952, in each instance. The retractor possesses a handle region configured as a shaft, followed by a head region having a concave curvature. The curvature of the head region can correspond to the curvature of the eye socket floor.

A spatula-shaped orbital retractor is shown in the brochure "Instrumentation for Fronto-Orbital and Anteroposterior Skull Base Procedures" from the company Howmedica Leibinger from the year 1996. This retractor comprises two identically shaped sheet-metal strips, which are rotatably connected with one another at a pivot point on their distal ends, facing away from the eye socket. During introduction into the eye socket, the two sheet-metal strips are disposed congruently one on top of the other ("introduction position"). Subsequent to introduction, the sheet-metal strips are then pivoted about their common pivot point by means of a pushing movement, and thereby brought into a retraction position. The congruency of the sheet-metal strips in the introduction position facilitates introduction of the retractor into the eye socket, while a greater effective surface for retraction is available in the retraction position, because of the pivoted sheet-metal strips.

A similar spatula-shaped retractor is known from the Rapid Response program of the company Biomet Microfixation ("Fernandes Orbital Retractor"). This retractor also comprises two sheet-metal strips, which are pivoted by means of a screw mechanism and thereby brought into the retraction position. In contrast to the Stryker retractor, the pivot point of the Biomet Retractor is disposed at the proximal end, in other words the end of the sheet-metal strips facing the eye socket.

There is a need for a retractor that is simple to operate, for use in a surgical operation in the region of an eye socket.

BRIEF SUMMARY OF THE INVENTION

A retractor for use in a surgical operation in the region of an eye socket is proposed, which comprises at least two retraction elements configured in area-covering manner as well as at least one spring element. The retraction elements can be moved relative to one another, between an introduction position having a first surface coverage and a retraction position having a second surface coverage that is smaller than the first surface coverage, where the spring element makes available a pre-tension that forces the retraction elements into the retraction position.

The retraction elements configured in area-covering manner can have a planar (in other words level) or a non-planar (in other words curved, for example) shape. Also, it is possible that the retraction elements comprise a combination of planar and non-planar surfaces.

The mobility of the retraction elements can be selected in such a manner that the spring element is able to force the retraction elements against a region of the eye socket in the retraction position (for example against an inner region or a delimitation of the eye socket). For this purpose, a cross-section of a surface area defined by the retraction elements in the retraction position can be greater than a corresponding cross-section of the eye socket. In this manner, jamming accommodation of the retraction elements in the eye socket, for example, can be brought about.

The retraction elements can be dimensioned in such a manner that they are accommodated essentially completely in the eye socket. Only at least one fastening section, for example, which connects the retraction elements with a handle region of the retractor, can be excepted from complete accommodation. In contrast, the effective surface area of the retraction elements does not demonstrate any projection beyond the eye socket (i.e. out of the eye socket).

As far as the shaping of the retraction elements is concerned, different configurations are possible. For example, the individual retraction elements can all have essentially the same shape, or they can have different shapes. In one embodiment, the retraction elements run together at an acute angle in the direction of the interior of the eye socket. Additionally or alternatively, it is possible that the retraction elements, in their entirety, define a leaf-shaped surface in the retraction position, which surface can be accommodated completely in the eye socket, as already explained above. The leaf-shaped surface can make a transition into a fastening section, by way of an incision, by means of which section the retraction elements are connected with a handle region of the retractor. The position of the incision can be selected in such a manner that (in the retraction position) it is disposed in the region of the outer delimitation of the eye socket.

The retractor can furthermore comprise an activation device that is configured to move the retraction elements from the retraction position into the introduction position, overcoming the pre-tension. It is practical if the activation device can be moved (at least essentially) in translational manner. However, it could also be moved in rotational or another manner.

In addition to the activation device, the retractor can comprise a handle region, where it is practical if the activation device is disposed in the handle region. The handle region can be formed by a single handle part or by multiple handle parts. According to one implementation, the handle region comprises two handle parts that can be moved (for example pivoted) relative to one another, which parts jointly form the activation device. In this connection, each handle part can be coupled with one of the retraction elements, in each instance, in articulated manner.

The handle parts can be coupled with one another by way of an articulation or in another manner. In this connection, the spring element can be disposed in the coupling region, or can actually form the coupling. According to a first embodiment, the distal sections of the handle parts, which face away from the eye socket, are coupled with one another (for example in the manner of a pair of tweezers). According to a second embodiment, central sections of the handle parts are coupled with one another (for example in the manner of a pair of scissors or tongs).

According to a further embodiment, the activation device comprises a pushing element that is coupled with at least one of the retraction elements in articulated manner. This coupling can take place by way of a gear mechanism, which converts a translational movement of the pushing element into a pivoting movement or other type of movement of the retraction element. The gear mechanism can comprise a scissors mechanism.

The retraction elements can be movable relative to one another about a common pivot point. In this connection, the pivot point can be provided at a proximal end of the retraction elements, facing the eye socket. Furthermore, the pivot point can be predetermined in defined manner, for example by means of a bearing (for example an articulation).

The retraction elements can have a flat or curved shape, in each instance. In the case of a curved structure, the retraction elements can jointly define a concave curved surface, for example in the manner of a spoon (at least in the retraction position). The curvature of this surface can approximately coincide with the curvature of the floor of the eye socket.

In addition, the retractor can comprise a device for guiding and/or limiting the movement of the retraction elements. This device can be brought about, for example, by means of engagement of a pin fastened onto a first retraction element in a groove that is configured in a second retraction element.

BRIEF DESCRIPTION OF THE DRAWINGS

Further advantages, details, and technical characteristics of the retractor presented here are evident from the following description of the exemplary embodiments, making reference to the drawings. These show.

DETAILED DESCRIPTION

Figure 2:
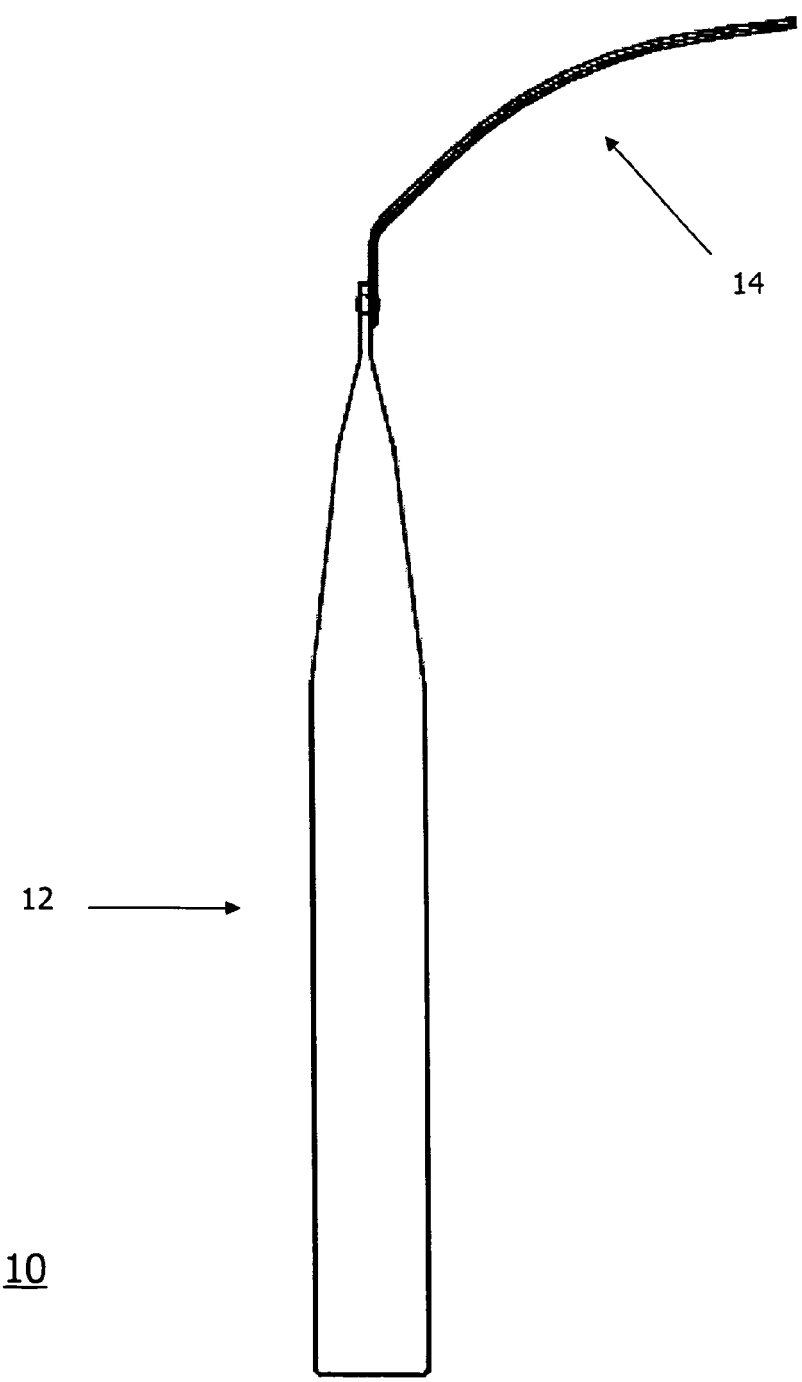
FIG. 2 is a side view of the orbital retractor according to FIG. 1.
Figures 3A, 3B:
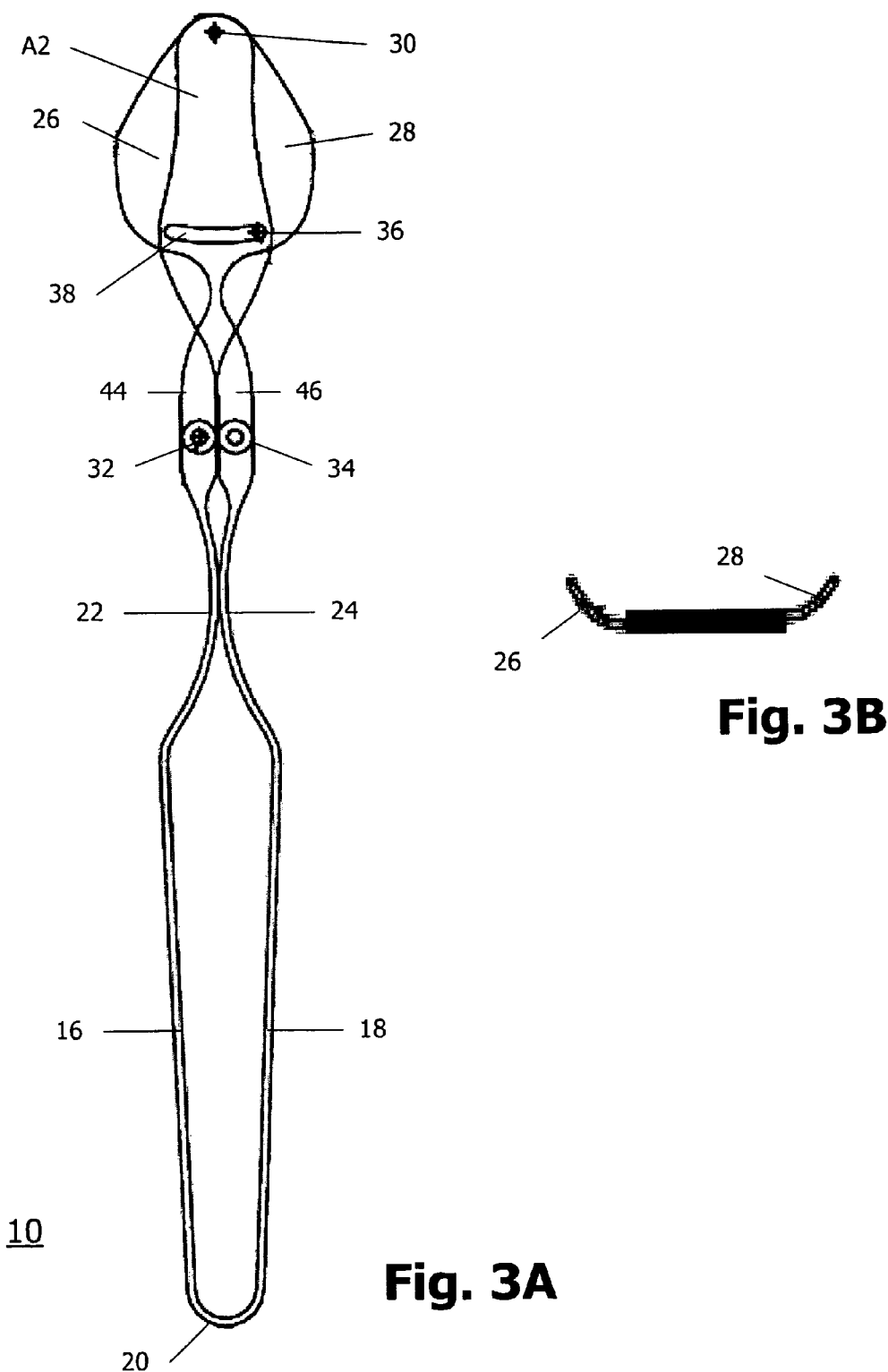
FIGS. 3A and 3B is a top view as well as a front view of the orbital retractor according to FIG. 1 in an introduction position (activation position)

In the following, a first exemplary embodiment of an orbital retractor 10 will be explained first, making reference to FIGS. 1 to 3. In this connection, FIGS. 1 and 2 show the retractor 10 in a non-activated basic position (retraction position), while FIGS. 3A and 3B illustrate the retractor 10 in an activated position (introduction position).

The retractor 10 comprises a distal handle region 12, facing away from the eye socket, as well as a proximal head region 14, facing the eye socket. The handle region 12 is configured in the manner of a pair of tweezers, and comprises two handle parts 16, 18, which are coupled with one another at their distal ends by way of a connection point 20.

Figure 1:
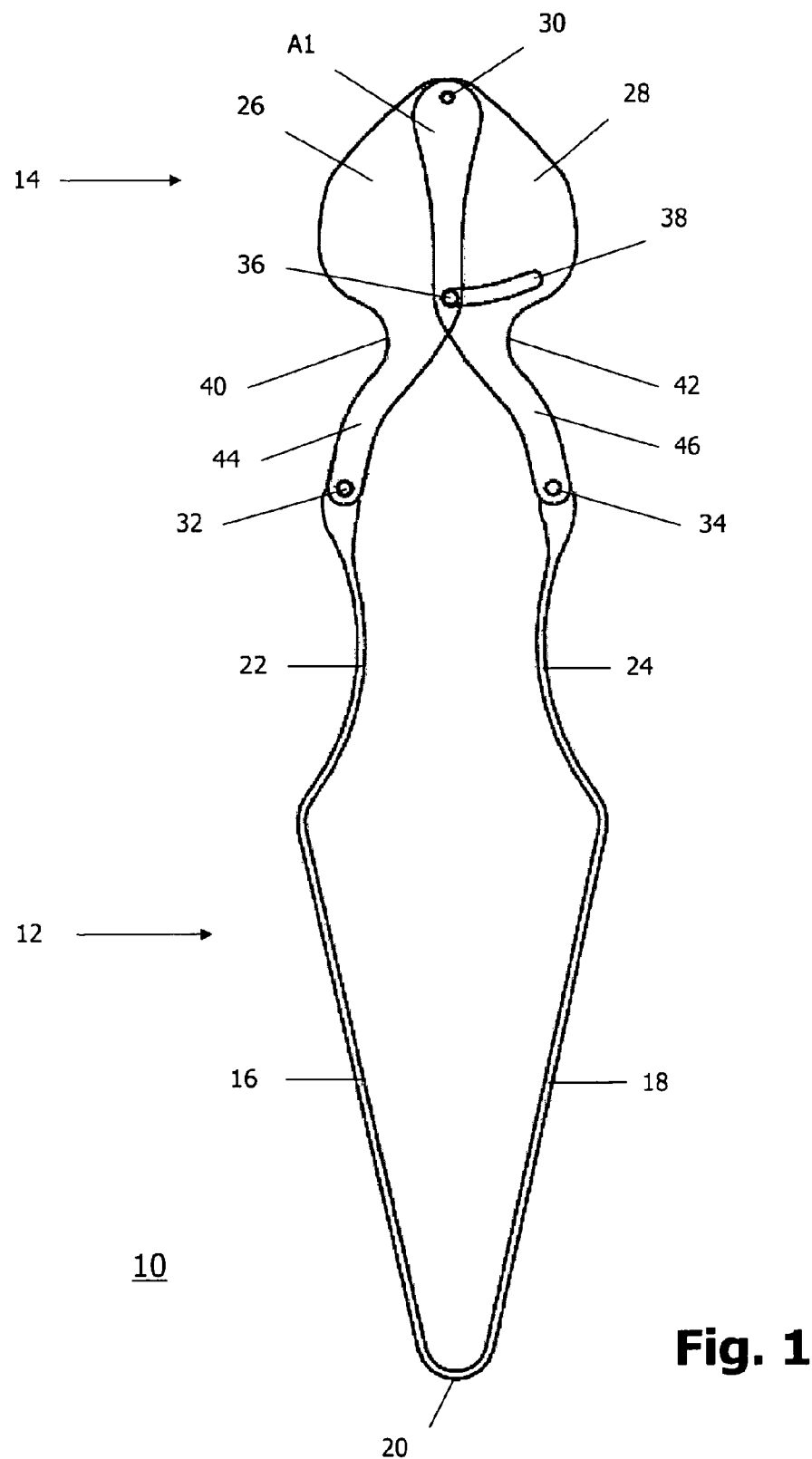
FIG. 1 is a top view of a first exemplary embodiment of an orbital retractor in a retraction position (basic position)

The two handle parts 16, 18 form an activation device for bringing the retractor 10 from the retraction position shown in FIG. 1 into the introduction position shown in FIG. 3.

The handle parts 16, 18 as well as the connection point 20 are configured in one piece and were formed by means of bending a single sheet-metal strip having resilient properties. Because of the resilient properties of the sheet-metal strip, the connection point 20 acts as a spring element, which makes a pre-tension available in the state illustrated in FIG. 1. This pre-tension forces the two handle parts 16, 18 away from one another about the connection point 20.

In an alternative exemplary embodiment, the connection point 20 between the two handle parts 16, 18 is implemented by means of an articulation (e.g. by means of a hinge). In this case, the pre-tension can be made available by a pressure spring disposed in the region of the articulation between the two handle parts 16, 18.

Each of the two handle parts 16, 18 possesses a handle depression 22, 24 in a central section. The handle depressions 22, 24 make a transition, at their proximal ends, into fastening sections set crosswise by 90°, in which the handle region 12 is connected with the head region 14.

The head region 14 comprises two retraction elements 26, 28 configured in area-covering manner, made of thin sheet metal. The two retraction elements 26, 28 are connected with one another at their proximal ends, at a common pivot point 30, and are mounted to as to pivot or rotate about this pivot point 30, relative to one another. Furthermore, the two retraction elements are coupled, at their distal ends, with the two handle parts 16, 18, by way of an articulation 32, 34, in each instance. Because of this coupling of the two retraction elements 26, 28 with the handle region 12, the pre-tension that acts on the handle parts 16, 18 brings about pivoting open (or "fanning") of the two retraction elements relative to one another, about the pivot point 30. The pre-tension therefore forces the retraction elements 26, 28 into the retraction position illustrated in FIG. 1.

The pivoting movement of the two retraction elements 26, 28 relative to one another, about the pivot point 30, is restricted by a device configured in the region of the retraction elements 26, 28. This device comprises a pin 36 fastened onto the retraction element 26 approximately in the center, which pin engages into a groove 38 configured in the retraction element 28. In the retraction position illustrated in FIG. 1, pivoting of the two retraction elements 26, 28 is restricted in that the pin 36 makes contact with the left end of the groove 38. In addition to this limiting function, the interaction of the pin 36 with the groove 38 also brings about guidance of the pivoting movement of the two retraction elements 26, 28 relative to one another about the pivot point 30.

In order to bring the retractor 10 from the basic position according to FIG. 1 into its introduction position shown in FIG. 3, the two handle parts 16, 18 must be translationally moved toward one another (in the manner of the handle parts of a pair of tweezers), overcoming the pre-tension, until the pin 36 comes to lie against the right end of the groove 38 in FIG. 3 (or the two handle depressions 22, 24 touch one another). As a comparison of the two FIGS. 1 and 3A shows, the surface coverage (overlap) A1 of the two retraction elements 26, 28 in the retraction position according to FIG. 1 is smaller than the surface overlap A2 of the two retraction elements 26, 28 in the introduction position. In other words, the effective surface area defined by the two retraction elements 26, 28 in the introduction position according to FIG. 3 is smaller than in the retraction position according to FIG. 1. In the introduction position, introduction of the reactor 10 into the eye socket is facilitated because of the resulting smaller (maximal) surface area cross-section, while in the retraction position, a greater effective surface area for the intended retraction purposes is available.

As illustrated in FIGS. 1 and 3A, each of the two retraction elements 26, 28 possesses the shape of half a leaf, which runs to a point in the direction of the common pivot point 30. In their totality, the two retraction elements 26, 28 therefore form a leaf-shaped surface that possesses a greater surface content in the retraction position than in the introduction position. The leaf-shaped surface makes a transition, by way of lateral incisions 40, 42, into two narrow, post-shaped fastening sections 44, 46. The distal end of each fastening section 44, 46 is coupled with the fastening section of the related handle part 16, 18, by way of the related articulation 32, 34.

The maximal cross-section of the leaf-shaped surface in the introduction position can amount to approximately 1 to 3 cm (for example approximately 1.5 to 2.5 cm), and can become larger in the retraction position, to approximately 2 to 5 cm (for example approximately 3 to 4 cm). The length of the leaf-shaped surface can be selected in such a manner that the surface can be completely introduced into the eye socket in the retraction position (i.e. it can lie between 1.5 and 3.5 cm, for example). The length of the handle part 10 can lie in the range between approximately 8 and approximately 15 cm (for example approximately 10 to 12 cm).

As the side view of the retractor 10 according to FIG. 2 illustrates, the retraction elements 26, 28 can be angled away with reference to the handle region 12, in their fastening sections 44, 46. This angling away facilitates handling of the retractor 10 and, in particular, introduction of the retractor 10 into the eye socket. As FIG. 3B further illustrates, each of the two retraction elements 26, 28 is angled away toward the top laterally on the outside. The retraction elements 26, 28 therefore jointly define a concave curved surface that supports the retraction function.

The concave curvature can correspond to the curvature of the eye socket.

Figure 4:
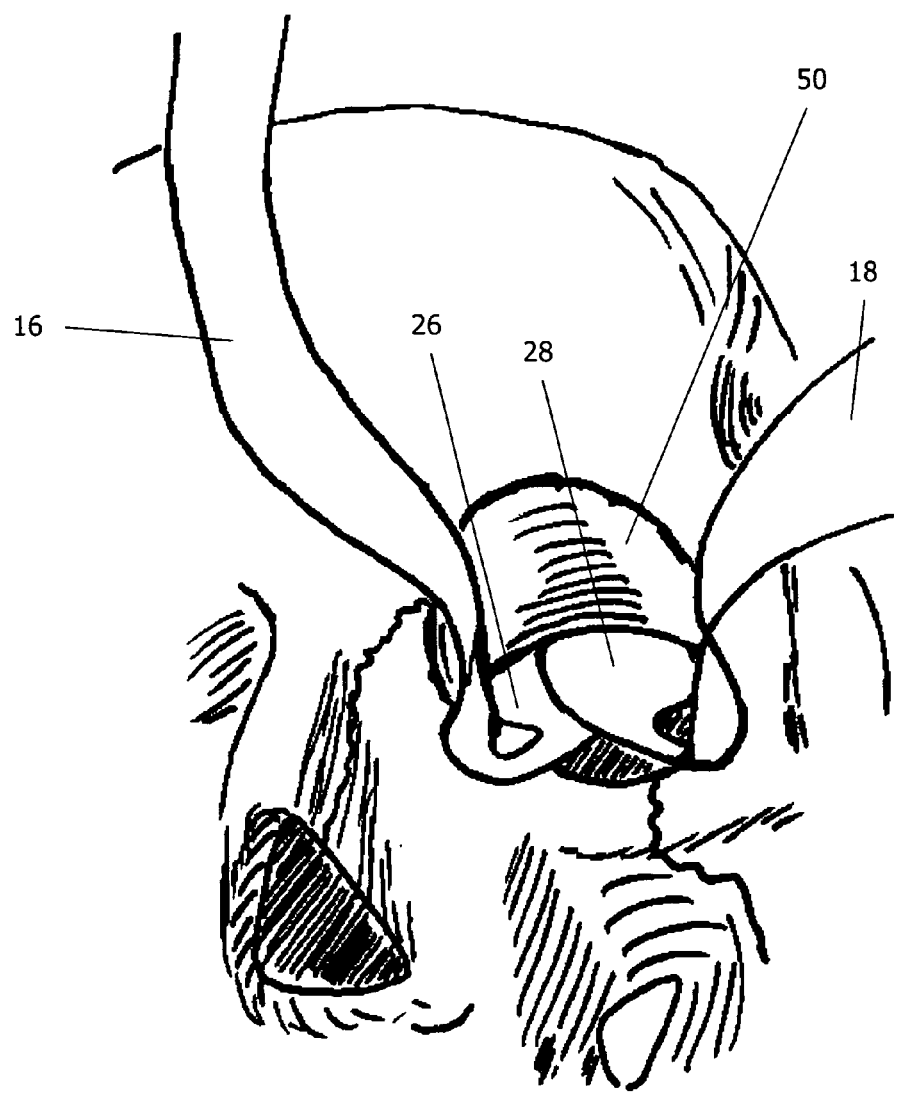
FIG. 4 is a further exemplary embodiment of an orbital retractor in a perspective view, in a state in which it is introduced into the eye socket.

FIG. 4 shows a further exemplary embodiment of an orbital retractor 10 in a perspective view. The retractor 10 according to FIG. 4 is in a state in which it has been introduced into an eye socket 50, and has the same functions as the orbital retractor described with reference to FIGS. 1 to 3. For this reason, the following functional explanations also apply to the retractor described above.

In a design aspect, a first deviation between the orbital retractor 10 according to FIG. 4 and the retractor described above consists in that the retractor 10 according to FIG. 4 is produced from a single sheet-metal part (again bent in the manner of a pair of tweezers). Furthermore, the restriction/guidance device (composed of pin 36 and groove 38 according to FIG. 1) was left out, as was the common mounting of the retraction elements 26, 28 on a proximal pivot point (reference symbol 30 in FIG. 1).

Within the scope of a surgical operation, first a small incision is made in the region of a lower section of the opening of the eye socket, which incision is just sufficient to place the retraction elements 26, 28, in the introduction position (analogous to FIG. 3) into the eye socket 50. In this connection, the retraction elements 26, 28 are dimensioned in such a manner that they can be accommodated essentially completely (with the exception of the fastening sections 44, 46) in the eye socket 50 (cf. FIG. 4). Thereupon the retraction elements 26, 28 are introduced into the eye socket 50 by way of the incision. Subsequently, the force applied to the handle parts 16, 18 by the surgeon is reduced, so that the retraction elements 26, 28 are forced into the retraction position illustrated in FIG. 4, as the result of the inherent pre-tension. In this connection, the handle parts 16, 18 perform a translational movement.

As soon as the retraction elements 26, 28 are in the retraction position, the retractor 10 can be used for its intended purpose. For example, the soft tissue filling the eye socket 10 can be pushed back to treat a fracture of the eye socket floor. Additionally or alternatively, the retractor 10 can also be used to push soft tissue back in advance of the incision, in order to keep the region intended for the incision clear.

The mobility of the retraction elements 26, 28 can be selected (for example by way of the length and position of the groove 38 according to FIGS. 1 to 3) in such a manner that the pre-tension is able to force the retraction elements 26, 28 against the interior of the eye socket 50 in the retraction position (cf. FIGS. 1 and 4). For this reason, a cross-section of the surface area defined by the retraction elements 26, 28 in the retraction position is greater than a corresponding cross-section of the eye socket. This leads to jamming of the retraction elements 26, 28 in the eye socket. Depending on the dimensioning of the pre-tension, a self-holding function of the retractor 10 in the eye socket 50 can be brought about or supported with this jamming.

As illustrated in FIG. 4, the incisions of the retraction elements 26, 28 are disposed in the region of the opening of the eye socket 50 in the retraction position. This measure supports essentially complete accommodation of the retraction elements 26, 28 in the eye socket 50 and facilitates access to the eye socket 50 by means of other surgical instruments.

Although the exemplary embodiments described possess an activation device for the retraction elements in the manner of the handle parts of a pair of tweezers, it is understood that other types of activation devices can also be used. For example, it is possible to implement the activation device by means of a handle region configured in the manner of a pair of tongs or scissors. In such an embodiment, a pressure spring or other type of spring element could be provided in an articulation region, which spring or element makes the pre-tension available for forcing the retraction elements into the retraction position. A person skilled in the art will furthermore be able, on the basis of his/her technical knowledge, to implement other types of activation devices for the retraction elements (for example on the basis of a pushing element acted on by spring force).

As is evident from the above description of exemplary embodiments, the orbital retractor presented here is easy to operate. Pre-tensioning of the retractor in the retraction position facilitates its user friendliness, because a surgeon can bring the retractor from its introduction position into the retraction position by simply reducing the activation source. The pre-tension can furthermore lead to jamming of the retraction elements within the eye socket, which stabilizes the position of the retractor. In an extreme case, it would be possible to implement a self-holding function for the retractor based on the pre-tension that is made available.

Furthermore, an embodiment in which the retraction elements are completely accommodated in the eye socket in the retraction position is advantageous, because in this manner, the retraction elements do not impair access to the eye socket for other types of surgical instruments. Furthermore, the access to the eye socket can be kept small by means of the retractor presented here (in other words no unnecessary widening is required).

It should also be noted that the device for guiding or limiting the movement of the retraction elements (composed of pin 36 and groove 38) could also be configured in other ways. In particular, it would be possible to provide this device on the retractor in such a manner that it lies outside the eye socket in the position in which the retraction elements have been introduced into the eye socket.

The invention claimed is:

1. A retractor for use in a surgical operation in the region of an eye socket, comprising:
    at least two retraction elements having overlapping facing surfaces configured in area-covering manner, which can be moved relative to one another between an introduction position having a first overlapping coverage area between the at least two retraction elements and a retraction position having a second overlapping coverage area between the at least two retraction elements configured in a manner that the second overlapping area is smaller than the first overlapping area between the at least two retraction elements configured in area-covering manner;
    at least one spring element that makes a pre-tension available that forces the retraction elements into the retraction position;
    an activation device that is configured to move the retraction elements from the retraction position into the introduction position, overcoming the pre-tension; and
    wherein in the introduction position at least a portion of the overlapping facing surfaces lie in parallel.

2. The retractor according to claim 1, wherein the mobility of the retraction elements is selected in such a manner that the spring element is able to force the retraction elements against a region of the eye socket in the retraction position.

3. The retractor according to claim 1, wherein the retraction elements are dimensioned so as to be accommodated in the eye socket essentially completely.

4. The retractor according to claim 1, wherein the retraction elements, in the retraction position, define a leaf-shaped surface that makes a transition into at least one fastening section, by way of an incision.

5. The retractor according to claim 1, wherein the activation device can be moved essentially translationally.

6. The retractor according to claim 5, further comprising a handle region, wherein the activation device is disposed in the handle region.

7. The retractor according to claim 6, wherein the handle region comprises two handle parts that can be moved relative to one another, which form the activation device.

8. The retractor according to claim 7, wherein each handle part is coupled with one of the retraction elements, in each instance, in articulated manner.

9. The retractor according to claim 8, wherein the handle parts are coupled with one another.

10. The retractor according to claim 9, wherein the spring element is disposed in the region of the coupling or forms the coupling.

11. The retractor according to claim 10, wherein distal sections of the handle parts, facing away from the eye socket, are coupled with one another.

12. The retractor according to claim 10, wherein central sections of the handle parts are coupled with one another.

13. The retractor according to claim 1, wherein the activation device comprises a pushing element that is coupled with at least one of the retraction elements, in articulated manner.

14. The retractor according to claim 1, wherein the retraction elements can be moved relative to one another, about a common pivot point.

15. The retractor according to claim 14, wherein the pivot point is provided at a proximal end of the retraction elements, facing the eye socket.

16. The retractor according to claim 1, wherein the retraction elements jointly define a concave curved surface.

17. The retractor according to claim 1, further comprising a device for guiding and/or limiting the movement of the retraction elements.

18. A retractor for use in a surgical operation in the region of an eye socket comprising:
    a first arm portion and a second arm portion pivotally connected to each other adjacent a first end of each arm portion, the first and second arm portions having overlapping facing surfaces, at least a portion of the overlapping facing surfaces lying in parallel, the first arm portion including a pin and the second arm portion including an arcuate slot for slidably receiving the pin, the first and second arm portions each having a second end and a spring extending between the first and second arm second ends for pivoting the first and second arm portions overlapping surfaces from a position of maximum overlap to a position of minimum overlap determined by the contact of the pin with ends of the slot, the pivoting of the first and second arm portions causes the portions of the overlapping surfaces to move in parallel.

19. The retractor as set forth in claim 18 wherein the spring comprises first and second leg portions jointed together at a first end of each leg portion and respectively attached to the first and second arm portions second ends at a second end of each leg portion.

20. A retractor for use in a surgical operation in the region of an eye socket, comprising:
    at least two retraction elements having overlapping facing surfaces configured in area-covering manner, which can be moved relative to one another between an introduction position having a first overlapping coverage area between the at least two retraction elements and a retraction position having a second overlapping coverage area between the at least two retraction elements configured in a manner that the second overlapping area is smaller than the first overlapping area between the at least two retraction elements configured in area-covering manner;
    at least one spring element that makes a pre-tension available that forces the retraction elements into the retraction position;
    wherein in the introduction position at least a portion of the overlapping facing surfaces lie in parallel; and
    wherein the retraction elements, in the retraction position, define a leaf-shaped surface that makes a transition into at least one fastening section, by way of an incision.

* * * * *